United States Patent [19]

Ladd

[11] Patent Number: 5,050,109

[45] Date of Patent: Sep. 17, 1991

[54] METHOD AND APPARATUS FOR MEASURING THE HUMIDITY OF AMBIENT AIR SURROUNDING AN AIRCRAFT IN FLIGHT

[75] Inventor: Michael M. Ladd, Renton, Wash.

[73] Assignee: The Boeing Company, Seattle, Wash.

[21] Appl. No.: 452,817

[22] Filed: Dec. 19, 1989

[51] Int. Cl.$^5$ ............................................. G01N 5/02
[52] U.S. Cl. ....................................... 364/556; 73/76;
73/29.01; 364/423
[58] Field of Search ................... 364/556, 550, 551.01,
364/423; 340/962; 73/73, 76, 77, 29.01

[56] References Cited

U.S. PATENT DOCUMENTS

| | | | |
|---|---|---|---|
| 2,485,522 | 10/1949 | Anderson | 62/150 |
| 2,699,537 | 1/1955 | Sederstrom | 417/18 |
| 2,777,301 | 1/1957 | Kuhn | 62/178 |
| 2,835,340 | 5/1958 | McGuff et al. | 55/82 |
| 2,836,057 | 5/1958 | Johnson et al. | 73/29.03 |
| 2,867,989 | 1/1959 | McGuff | 62/150 |
| 3,083,546 | 4/1963 | Turek | 62/150 |
| 3,463,000 | 8/1969 | Broadwin | 73/76 |
| 3,514,994 | 6/1970 | Shaw | 73/76 |
| 3,981,466 | 9/1976 | Shah | 244/134R |
| 4,688,418 | 8/1987 | Cheung et al. | 73/29 |
| 4,799,376 | 1/1989 | Siedlecki, Jr. et al. | 73/29 |
| 4,864,844 | 9/1989 | Moritz | 73/29 |

FOREIGN PATENT DOCUMENTS 2112857 11/1971 Fed. Rep. of Germany ...... 340/962

Primary Examiner—Joseph L. Dixon
Attorney, Agent, or Firm—Seed and Berry

[57] ABSTRACT

An apparatus and method of determining the humidity of ambient air surrounding an aircraft in flight are disclosed. Air is captured as the aircraft flies. Measurements for calculating the mass flow rate of the captured air are made. The captured air is dehumidified in a moisture extractor. A flow of moisture and aa flow of dehumidified air exit from the water extractor. The mass flow rate of the moisture exiting from the moisture extractor is measured. The humidity of the captured air is calculated based on the respective mass flows and the efficiency of the moisture extractor. Because the mass flow measurements and the efficiency of the moisture extractor depend, in part, on the humidity of the captured air, an assumed humidity value is used at the beginning of the calculations. The assumed humidity is compared to the calculated humidity. If the newly calculated humidity is approximately equal to that used in the calculations, the value is output as the humidity of ambient air. If they are not approximately equal, the calculations are repeated until the calculated humidity value and the assumed humidity value are approximately equal. As the aircaft flies, new ambient air is constantly capatured, measurements are made, and the humidity value is recalculated. The crew and equipment are thus provided with an accurate and constantly updated humidity value of ambient air during the flight.

26 Claims, 6 Drawing Sheets

METHOD AND APPARATUS FOR MEASURING THE HUMIDITY OF AMBIENT AIR SURROUNDING AN AIRCRAFT IN FLIGHT

TECHNICAL FIELD

This invention relates to measuring humidity and, more particularly, to a method and apparatus for measuring the humidity of ambient air around an aircraft while in flight.

BACKGROUND OF THE INVENTION

Accurately knowing the humidity of ambient air surrounding an aircraft in flight is advantageous for many reasons. Icing conditions can be more accurately predicted based on ambient humidity. The crew can thus be alerted to turn on or off anti-icing systems. The humidity of ambient air also affects the operation of some military equipment. Accurately knowing the humidity aids the crews in carrying out a military flight mission.

Current methods of measuring ambient humidity are not suitable for measuring humidity of ambient air surrounding an aircraft in flight. One current method is to measure fiber expansion/contraction changes due to moisture absorption. Another current method is to measure the infrared energy attenuation in ambient air. Other methods are used by meteorologists, as is known in the art. Most of the current methods rely on the measuring devices being stationary. However, for an aircraft in flight, ambient air is passing by rapidly, often at supersonic speeds, thus preventing the use of conventional measuring devices. In addition, an aircraft in flight frequently changes altitude and rapidly passes through bands of air having radically different humidities from each other. The humidity of ambient air must be accurately known very quickly to be useful to the crew. Consequently, none of the current methods are sufficiently accurate or rapid for measuring ambient humidity for an aircraft while in flight.

SUMMARY OF THE INVENTION

It is therefore an object of this invention to provide a method of accurately and rapidly determining the humidity of ambient air surrounding an aircraft while in flight.

It is another object of this invention to provide an apparatus for measuring the humidity of ambient air around an aircraft while in flight.

These, and other objects of the invention, as will be apparent herein, are accomplished by capturing a flow of ambient air during flight. Measurements are taken to calculate the mass flow of the captured ambient air. Moisture is extracted from the captured airflow in a water extractor. Flow streams of moisture and dehumidified air exit from the water extractor. The mass flow rate of the extracted moisture and, optionally, of the dehumidified air, are measured and stored. The humidity of the captured air is calculated based on the mass flow rates into and out of the water extractor and the efficiency of the water extractor.

Calculating the humidity may require numerous iterations and recalculations. Accurate measurements of an air mass flow rate require that the density of the air be known. However, the density of air is proportional to the humidity, which is the property to be measured. In addition, water extractor efficiency varies with the humidity and the mass flow rate. Thus, a value of the property to be measured, humidity, must be provided to accurately calculate the humidity. According to the invention, a humidity value is assumed for the initial calculation of captured air mass flow and water extractor efficiency. The humidity is then calculated based on this assumed humidity. The calculated humidity is compared to the assumed humidity. If they are approximately equal, the calculated humidity value is output as the current humidity value. If they are not approximately equal, the just-calculated humidity value becomes the assumed humidity value and is used to determine a new value for the captured air mass flow and the extractor efficiency. The humidity is recalculated based on the new values for the captured air mass flow and extractor efficiency. The newly calculated humidity is again compared to the assumed humidity value to determine if they are equal. If they are not approximately equal, the substitution and recalculation continues until the calculated humidity value and the assumed humidity value converge to be approximately equal.

An alternative method of ensuring that the calculated humidity value is correct is to continue the humidity calculation until the two most recent captured air mass flow calculations converge. The sum of the dehumidified mass flow rate and extracted moisture mass flow rates can also be compared to the captured mass flow as a cross-check for assurance that the humidity value is accurate. In one embodiment, the mass flow rate calculation is performed only once using an assumed humidity value and the recalculations only take into account the variation in water extraction efficiency based on changes in humidity. In an alternative embodiment, no alterations or recalculations are performed; the humidity value is accepted as correct after one pass through the calculations.

Accurate ambient humidity measurements are provided rapidly because the calculations are performed using stored values and a microprocessor. The ambient humidity values are updated as frequently as necessary, many times per second if desired. The most recently calculated humidity value is used for the assumed humidity value in subsequent calculations, decreasing the number of iterations necessary.

DETAILED DESCRIPTION OF THE INVENTION

Figure 1:
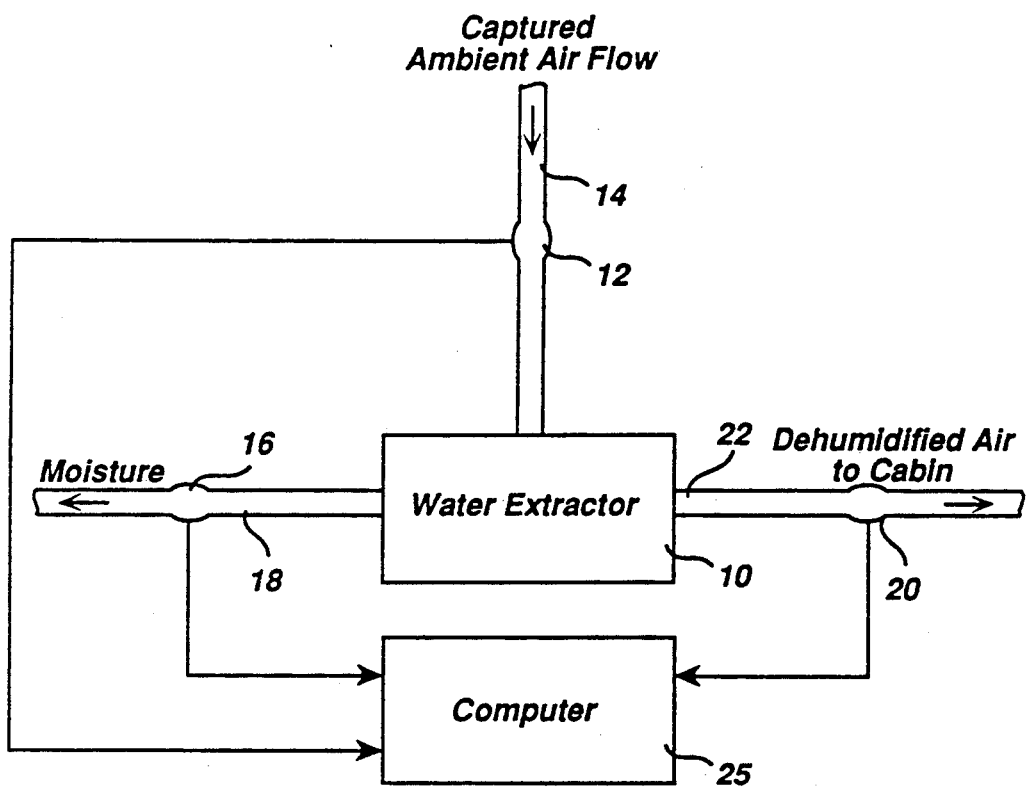
FIG. 1 is a schematic of an apparatus for carrying out the invention.

Most current aircraft include a water extractor to dehumidify the air prior to using it in the cabin or for aircraft functions. As shown in FIG. 1, ambient air 14 is captured from bleed air from an aircraft engine intake, from an auxiliary power system compressor, from bypass air, or the like and partially conditioned within air cycle machinery. The captured air 14 is separated by a water extractor 10 into moisture flow 18 and dehumidified airflow 22, which is provided to the cabin of the aircraft.

A mass flow meter 12 measures parameters in the captured air 14 for calculating its mass flow prior to passing through the water extractor 10. A mass flow meter 16 measures parameters in separated moisture flow 18 exiting the water extractor 10 for determining its mass flow. The moisture flow 18 may be all liquid, moisture-laden air or a combination thereof, depending on the type of water extractor 10 used. Dehumidified airflow 22 passes through mass flow meter 20, where measurements are made to determine its mass flow, and then to the cabin or equipment for use. Each of the individual components shown in FIG. 1 is known in the prior art. The water extractor 10 used in this invention is a conventional water extractor, dehumidifier, water separator, or the like of the type presently in use on any commercial or military aircraft. One water extractor 10 that has been found suitable for practicing the invention is sold by Garrett, under Part No. 194278-1.

The density of the air whose mass flow is being measured is a factor in determining the mass flow rate. The density of air varies as the humidity varies. In one embodiment, measurements from conventional air mass flow meters 12 and 20 are corrected based on changes in humidity. A density correction factor, $\sigma$, is calculated from the temperature and static pressure of air measured in the flow at the respective mass flow meter. The mass flow meters 12 and 20 include temperature and pressure sensors. The density correction factor, $\sigma$, for a given gas is given by the following equation:

$$\sigma = N * \frac{P}{T} \qquad (1)$$

where N is a calibration constant based on a given gas, P is the static air pressure in the flow meter and T is the air temperature in the flow meter. N is equal to $T_s/P_s$, where $T_s$ is the standard temperature and $P_s$ is the standard pressure of that gas at standard temperature. Thus, $\sigma$ is dimensionless, and if the air whose mass flow is being measured is at standard temperature and pressure, $\sigma$ equals 1. Variations from standard temperature and pressure are thus reflected in $\sigma$.

Because the air whose mass flow rate is being measured includes two gases whose concentration varies, water vapor and dry air, the density correction factor $\sigma$ is determined for each. For dry air, $$\sigma_a = N_a * \frac{P_a}{T_a} \qquad (2)$$

where $\sigma_a$ is the density correction factor for dry air, $N_a$ is the calibration constant for dry air, $P_a$ is the partial pressure of dry air in the mass flow being measured, and $T_a$ is the temperature of dry air in the mass flow being measured. For water vapor, $$\sigma_v = N_v * \frac{P_v}{T_v} \qquad (3)$$

where $\sigma_v$ is the density correction factor for water vapor, $N_v$ is the calibration constant for water vapor, $P_v$ is the partial pressure of water vapor in the mass flow being measured, and $T_v$ is the temperature of the water vapor in the mass flow being measured. The total density correction factor, $\sigma_t$, is the sum of the density correction factor for dry air and water vapor as given by equation 4:

$$\sigma_t = \sigma_a + \sigma_v \qquad (4)$$

To solve equations 2 and 3, the partial pressures of dry air and vapor must be provided. However, the pressure measured in the mass flow meter is the total static pressure. The partial pressures of dry air and water vapor are calculated from the following equations:

$$P_t = P_a + P_v \qquad (5)$$

where $P_t$ is the total static pressure, $P_a$ is the partial pressure of dry air, and $P_v$ is the partial pressure of water vapor. The partial pressure of the water vapor is calculated as follows:

$$P_v = P_a * \frac{H}{.622} \qquad (6)$$

where H is the humidity and 0.622 is the ratio of the molecular weight of water vapor to the molecular weight of dry air. $P_t$ is measured value and humidity value, $H_n$, is assumed in the first calculation, permitting equations 5 and 6 to be solved for both $P_v$ and $P_a$. The temperature of the air in the mass flow meter is measured and the temperatures of water vapor, $T_v$, and dry air, $T_a$, are assumed equal to the measured temperature (and equal to each other). Equations 2 and 3 are solved using the results from equations 5 and 6 and the measured temperature. The total density correction factor is then calculated according to equation 4. As the actual humidity value becomes known, it is substituted into equation 6 and the density correction factor is recalculated based on the current assumed humidity as explained in more detail herein. The calculation of the mass flow by the respective flow meters 12 and 20 is thus corrected based on the actual humidity and changes in humidity.

In pressure-sensing-type mass flow meters, the mass flow is determined by measuring the static pressure drop across an orifice. Static air pressure is measured on either side of an orifice and the temperature is measured on one side of the orifice. For such a flow meter, the mass flow rate is proportional to the log of the static pressure drop, corrected by $\sigma$. The mass flow M is given by $$M^n = K * \sigma * \Delta P \qquad (7)$$

where $\sigma$ is the total density correction factor calculated according to equation 4, $\Delta P$ is the drop in static pressure across the orifice, K is the calibrated constant, and n is the calibrated exponent. The values of K and n are different for each flow meter and system. To determine the exact mass flow rate constants k and n, the mass flow meter must be calibrated and the calibration constants determined. The mass flow meter is calibrated by measuring the exact mass flow for a given static pressure drop and $\sigma$. The mass flow rate based on changes in static pressure drop and $\sigma$ are plotted on a log-log graph. The slope of the line provides the calibration exponent, n, and the offset from the zero crossing of the mass flow rate provides a calibration constant, K. The calibrated mass flow meter is installed in the aircraft and mass flow M is calculated using equation 7.

In a radial flow-type mass flow meter, the radial velocity of a turbine rotated by the flow is measured to determine volumetric flow rate. The mass flow M is then given by the following equation:

$$M = K^* \sigma^* \omega \qquad (8)$$

where $\omega$ is the measured radial velocity of the turbine and $\sigma$, and K are the same factors, as described with respect to equation 7, and are determined using similar techniques as previously described, though the values may be different. A pressure and temperature sensor are within the radial flow-type meter to provide measurements for equations 1–6.

The mass flow of water is measured in flow meter 16. In one type of flow meter 16, the mass of water per unit of time is measured to provide the mass flow directly. In a radial velocity-type mass flow meter, the radial velocity of a rotating blade pushed by the flow of water is measured and the mass flow determined using equation 8.

The particular type of mass flow meter used for each flow determines the measurements that must be taken to measure mass flow accurately. Some types of mass flow meters, for example, those for water, may operate somewhat differently than other types, such as those for air. Some mass flow meters, such as for water or moisture-laden air, may not require density correction, pressure measurement, or the like, whereas such are required of most gas mass flow meters. Thus, the measurements to provide an accurate mass flow determination are those that are required by the type of mass flow meter used for meters 12, 16, and 20.

The measured values of pressure, temperature, and radial velocity (if a radial velocity flow is used) from the flow meters 12 and 20 are input to computer 25. Computer 25 includes a memory for storing the measured values, a processor for performing equations 1–8, look-up tables, and a program memory. The computer 25 repeatedly calculates humidity using equations 1–8 using the stored values from a single reading, as explained in more detail herein with respect to the flow chart of FIG. 3.

Figure 2:
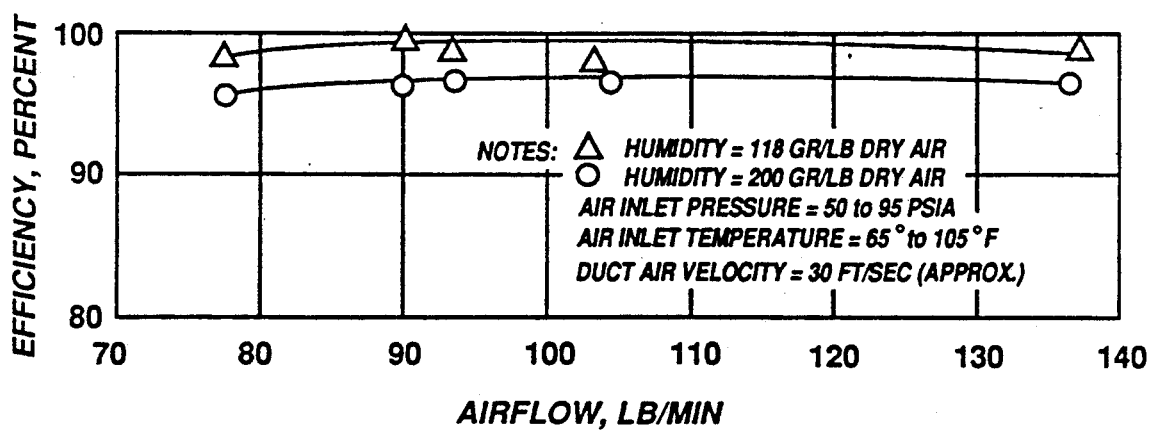
FIG. 2 is a graph plotting the efficiency of a sample water extractor according to the humidity and mass flow rate.

FIG. 2 is a graph of the efficiency of a suitable water extractor 10. The efficiency varies as a function of the mass airflow and the humidity of the incoming air. As the humidity of the air increases, the efficiency decreases. The extractor 10 has peak efficiency at about 110 pounds per minute. The extractor efficiency may also vary based on temperature, pressure, velocity and other factors which are measurable. The variation in efficiency of the particular water extractor used is stored in a look-up table. The manufacturer of each water extractor generally provides efficiency tables, which are used to generate the look-up table. The graph of FIG. 2 is based on a water extractor sold by Garrett under Part No. 194278-1.

Figure 3:
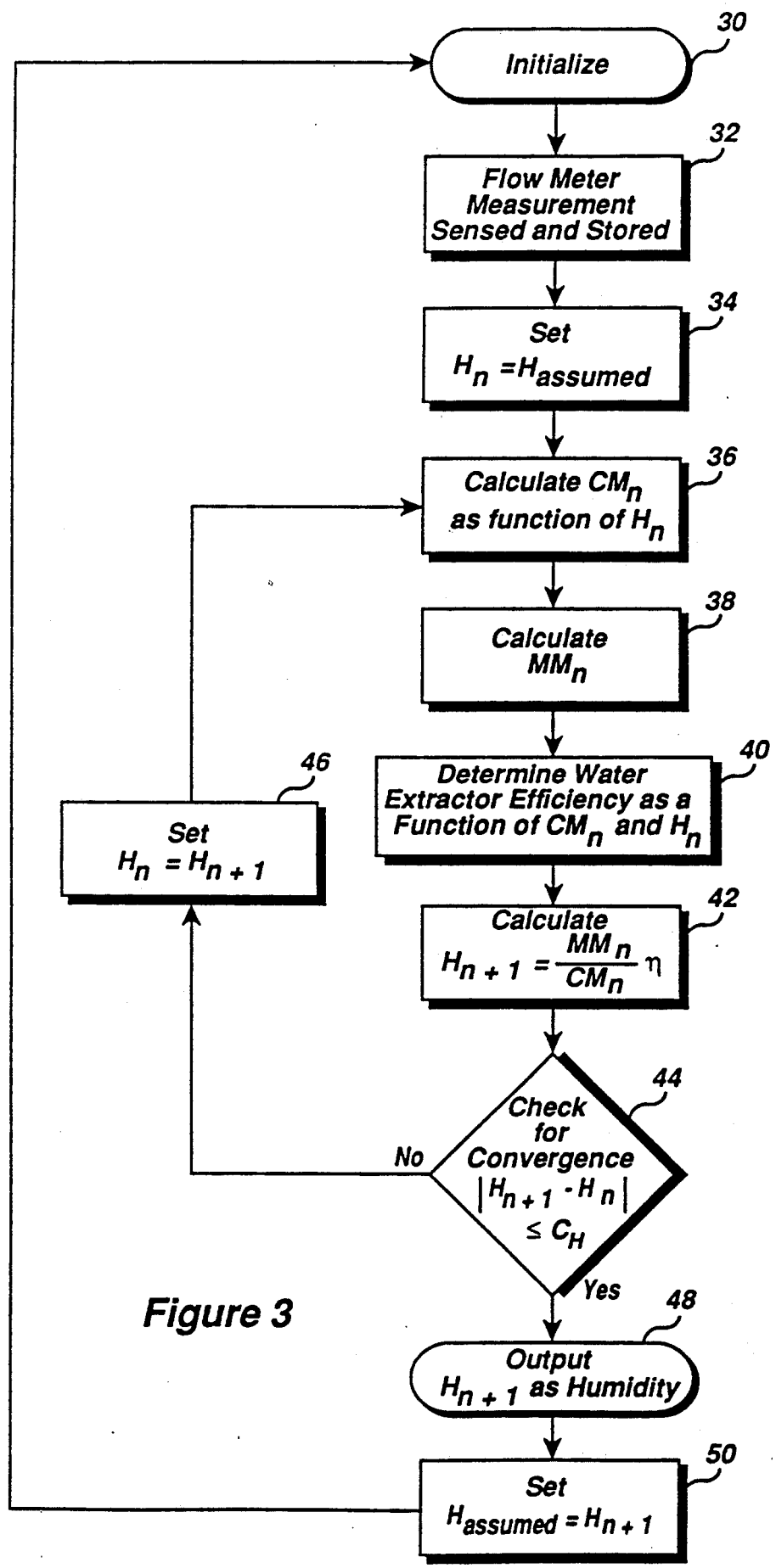
FIG. 3 is a flow chart of the steps followed in calculating humidity according to the invention.

The flow chart of FIG. 3 shows the program steps for computer software running on computer 25 of FIG. 1. In an initialization step 30, the equipment is prepared to begin a humidity measuring cycle. The control computer program is reset, initialized, and appropriate memories cleared. Flow meter measurements from flow meters 12, 16, and 20, including the temperature and pressure, are received and stored in the computer in step 32. The pressure in the flow meter 12 will generally be slightly higher than cabin pressure, possibly in the range of 10–12 psi. The captured air may go through several compression and decompression steps prior to entering flow meter 12. An assumed humidity value is selected and stored as the current humidity value, $H_n$, in step 34. Because the flow meter and water extractor calculations (equations 1–8 and FIG. 2) require a humidity value to provide an output, a humidity value is assumed for starting purposes only. If the flow meters and water extractor are of a type that do not require a humidity value to provide an output, this step in the process is eliminated.

The mass flow of the captured air $CM_n$ is then calculated, step 36, using $H_n$ as the humidity value in equation 6. Equations 2–5 are then solved based on the result of equation 6. The appropriate mass flow equation, whether 7 or 8, is then solved to determine $CM_n$. The present moisture mass flow $MM_n$ is determined in step 38 from the input of mass flow meter 16. $MM_n$ may or may not be a function of humidity of the moisture mass flow 18. The present water extractor efficiency, $\eta_n$, is then determined in step 40 from the look-up table based on the graph of FIG. 1 and the just-calculated mass flow $CM_n$. A humidity value of the captured air 14 is then calculated in step 42 according to the formula:

$$H_{n+1} = \eta_n * \frac{MM_n}{CM_n} \qquad (9)$$

The newly calculated humidity value, $H_{n+1}$, is compared in step 44 to the current humidity value $H_n$ to determine if they converge, that is, if they are approximately equal. If the absolute difference between the new humidity value $H_{n+1}$ and $H_n$ is less than a humidity convergence criteria, $C_H$, then the values are determined to be approximately equal and the new humidity value, $H_{n+1}$ is output as the current humidity in step 48. Usually, the newly calculated humidity value will not be approximately equal to the assumed humidity value on the first calculation. If the convergence criteria of step 44 is not met, the program returns to step 36 to perform the calculation again.

The newly calculated humidity value, $H_{n+1}$, is substituted as the present humidity value, $H_n$, in equation 6 in step 46 prior to steps 36–44 being repeated. The density correction factors $\sigma_v$ and $\sigma_a$ of equations 2 and 3 are recalculated and the total density correction factor, $\sigma_t$, is recalculated. The captured air mass flow, $CM_n$, is recalculated based on the new humidity value, as reflected in equation 7 or 8. The previously sensed and stored flow meter inputs are used to recalculate the present $CM_n$ and $MM_n$ as a function of the newly calculated humidity value. A new water extractor efficiency $\eta_{n+1}$ is calculated in step 40. The humidity is then recalculated based on the present values according to equation 9. The new humidity value is checked for convergence. The loop is repeated until the humidity value converges. That is, the just-calculated humidity value is substituted into equation 6 and all the values recalculated until the just-calculated humidity value, $H_{n+1}$, is approximately equal to the humidity value used in the calculations, $H_n$. If the first assumed humidity value is very different from the actual humidity value, several iterations may be required for the values to converge. Upon convergence, the final calculated humidity value is output as the humidity in step 48. The final humidity value is also stored as the assumed humidity value for the next humidity measurement in step 50. The calculations performed herein occur very rapidly under the control of the computer of FIG. 1. A single humidity value is calculated in less than microseconds, even though many iterations are performed on the stored values of captured air. The crew and operating equipment on the aircraft are thus provided with accurate humidity values of ambient air surrounding the aircraft during flight.

As the aircraft flies, new air enters the air mass flow meter 12. To calculate the humidity of the newly captured air, the program returns to step 30, new measurements are taken, and the humidity of current air is provided as described herein. Because the aircraft is flying through different zones of air very rapidly, recalculation of the current humidity by taking new measurements of the just captured air may occur frequently, one or more per second if desired.

Figure 4:
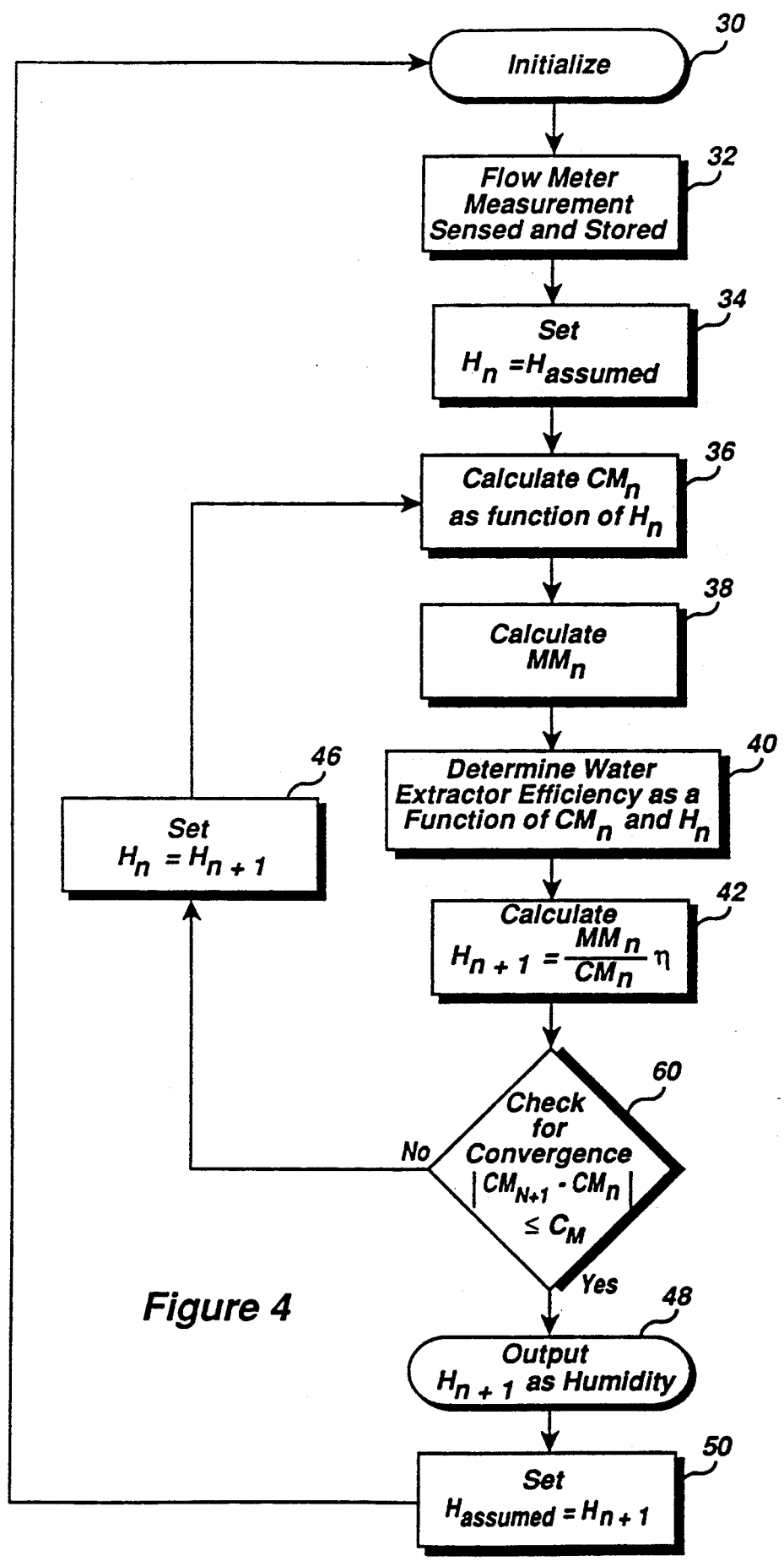
FIG. 4 is a flow chart of alternative steps in carrying out the invention.

FIG. 4 illustrates an alternative convergence criteria in step 60. All other steps remain the same. The present captured air mass flow, $CM_n$, can be checked against the just-calculated mass flow, $CM_{n+1}$, for convergence to determine if the calculated humidity value is correct. The just-calculated humidity value is output in step 48 if the mass flow values are within a convergence criteria of $C_m$ for the mass flow rate.

Figure 5:
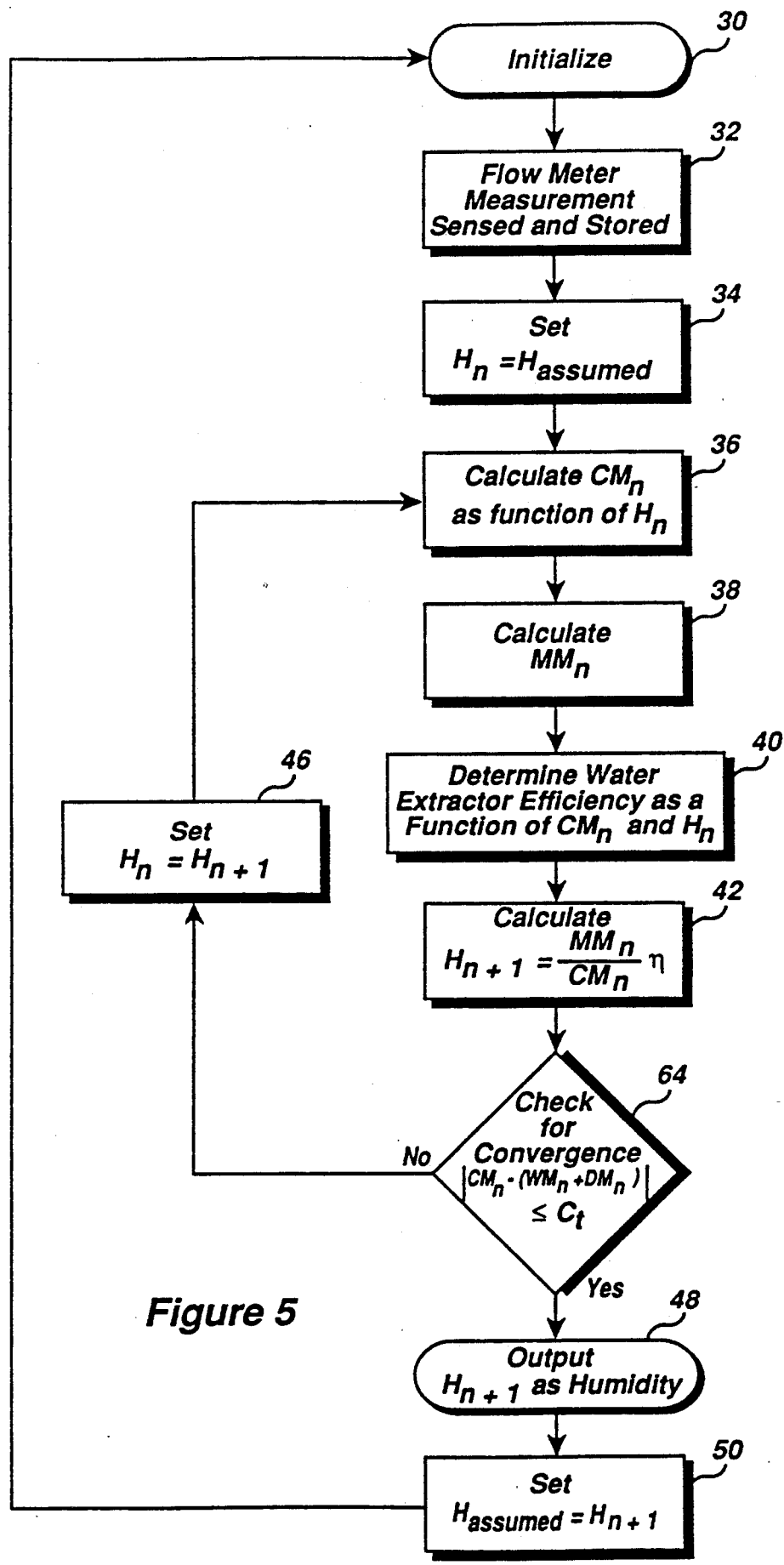
FIG. 5 is a flow chart of alternative steps followed in carrying out the invention.

FIG. 5 illustrates an alternative checking step 64. As a check, the total input can be compared with the total output. If the values are correct, the captured mass flow, $CM_n$, equals the sum of the moisture mass flow, $MM_n$, and the dehumidified mass flow, $DM_n$. The total values are compared in step 64 to determine if they are within a total convergence criteria, $C_t$. Step 64 may be carried out in addition to, or as a substitute for, steps 44 or 60.

Figure 6:
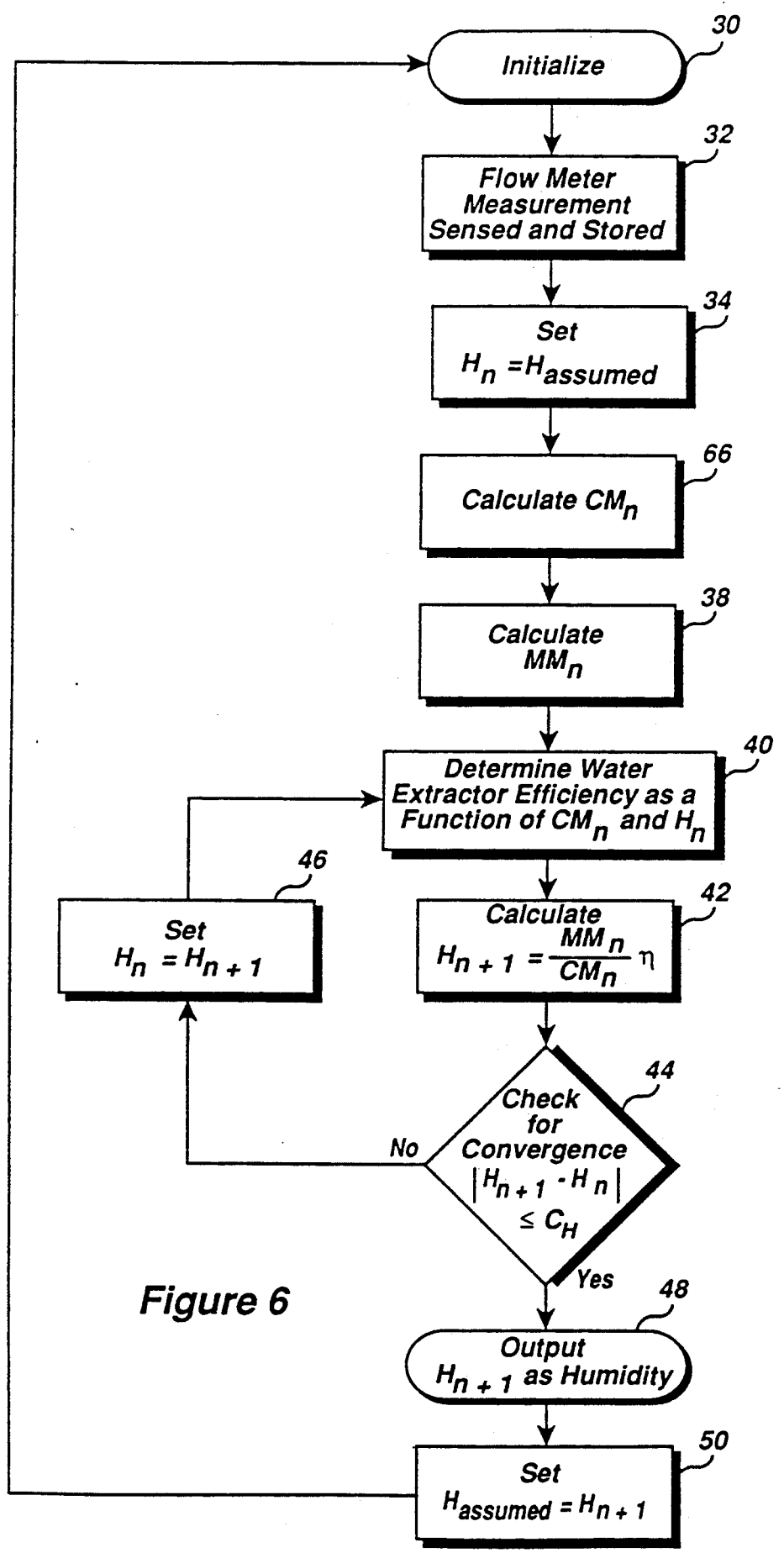
FIGS. 6 and 7 are flow charts of embodiments using an assumed humidity value.

Alternatively, the calculation of air mass flow in step 66 assumes zero humidity and is calculated based on equation 1 for dry air. The water extractor efficiency in step 40 is varied based on humidity and iterations are performed through the loop of step 46 until the humidity values converge as previously described. In some embodiments, the effect on air mass flow due to changes in humidity will be sufficiently low that assuming a single humidity value or, alternatively, no effect from humidity, is acceptable. Iterations and checking for convergence are required when the equations used to determine the humidity are based on the humidity. If the mass flow meters or equations selected for use to determine humidity do not also have humidity as a factor in the equation, iterations of the mass flow rate calculation may not be required to determine the humidity. In the embodiment of FIG. 6, a decision is made to use an assumed humidity value for the mass flow calculations and to not recalculate the air mass flow based on the true humidity.

Figure 7:
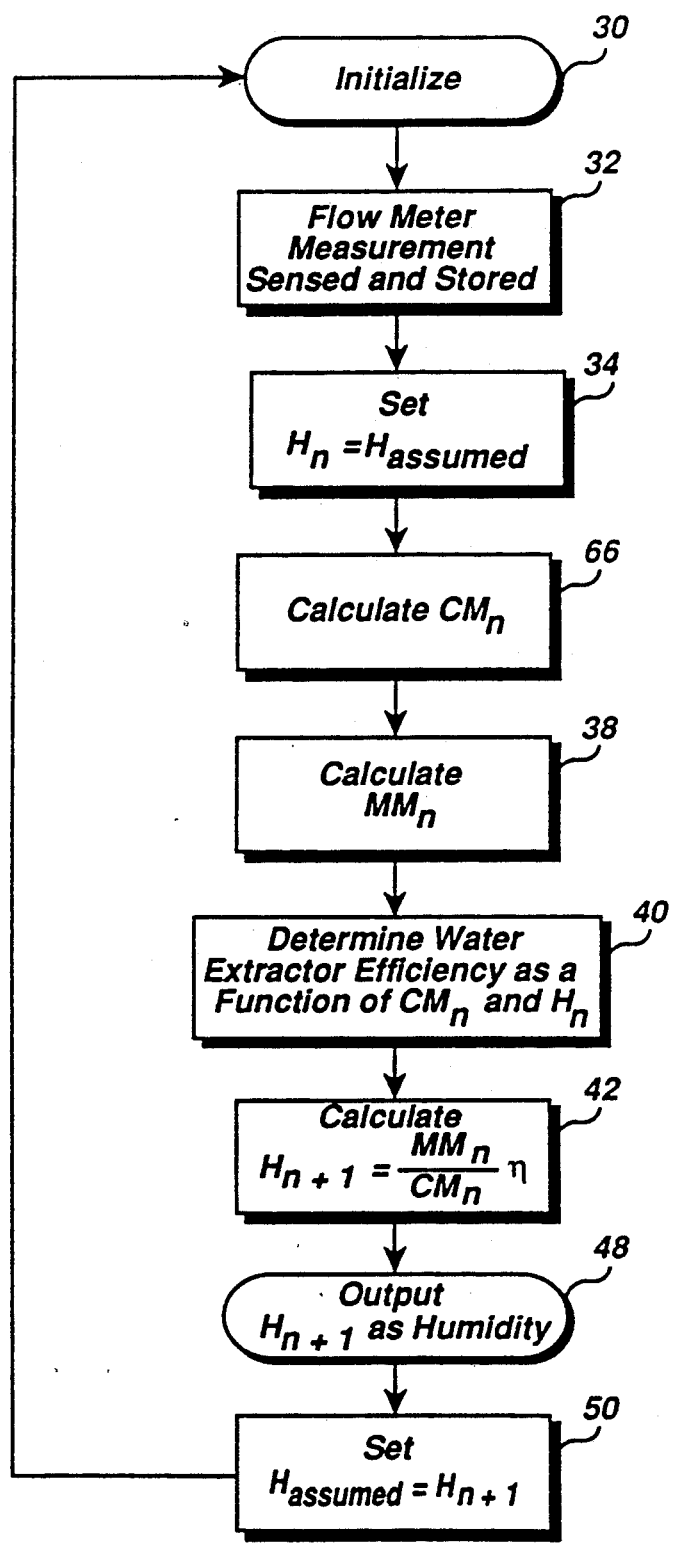

In the embodiment of FIG. 7, steps 44 and 46 of FIG. 6 are omitted and an assumed humidity value is used for all calculations and for the water extractor efficiency. No iterations are performed and the first calculated humidity is output as the humidity. Water extractor efficiency does not include variations based on humidity in one embodiment. The first calculated humidity value is accepted as the actual humidity value. To calculate a new humidity value, new measurements are taken in step 32 and the steps are repeated. The humidity will change as the aircraft flies into different zones of air.

I claim:

1. A method of calculating the ambient humidity of air surrounding an aircraft in flight, comprising the steps of:

capturing a flow of ambient air surrounding said aircraft during flight;
measuring selected parameters of said captured airflow to facilitate the calculation of a captured air mass flow rate;
storing said selected parameters;
calculating a captured air mass flow rate using said stored selected parameters;
extracting moisture from said captured airflow in a moisture extractor to separate said captured airflow into a moisture flow of said moisture extractor and a dehumidified airflow out of said moisture extractor;
calculating a moisture mass flow rate out of said moisture extractor;
calculating the humidity of said captured air using said captured air mass flow rate and said moisture mass flow rate; and
outputting said calculated humidity value.

2. The method according to claim 1 wherein said steps of calculating a captured air mass flow rate include the steps of:
assuming a first humidity value of said captured air;
calculating said captured air mass flow rate using said stored parameters and said assumed humidity value;
calculating a next humidity value;
comparing said next humidity value with said assumed humidity value; and
calculating said captured air mass flow rate using said stored parameters and said next humidity value if said next humidity value and said assumed humidity value are not approximately equal.

3. The method according to claim 2 wherein said next humidity value is output as the humidity value of said ambient air when said next humidity value and said assumed humidity value are approximately equal.

4. The method according to claim 1, further including:
measuring selected parameters of said dehumidified air to facilitate the calculation of said dehumidified air mass flow rate;
storing said selected parameters;
calculating said dehumidified air mass flow rate;
summing said dehumidified air mass flow rate and said moisture mass flow rate; and
outputting a signal if said sum is approximately equal to the mass flow rate of said captured air mass flow rate.

5. A method of calculating the ambient humidity of air surrounding an aircraft while in flight, comprising:
capturing a flow of ambient air surrounding said aircraft during flight;
storing a humidity value corresponding to an estimated humidity value of said ambient air;
determining the mass flow of said captured air using said stored humidity value as a factor in determining said captured air mass flow;
extracting moisture from said flow of captured air to provide a flow of moisture and a flow of dehumidified air;
determining the mass flow of said moisture extracted from said captured air;
calculating the humidity of said captured air using said determined mass flow rates of captured air and of extracted moisture as factors;
replacing said stored humidity value with said calculated humidity value;

redetermining said measured mass flow rate of captured air based on said calculated humidity value;

recalculating the humidity of said captured air using said recalculated measured captured air mass flow rate;

repeating said replacing, redetermining, and recalculating steps until said recalculated humidity value approximately equals said stored humidity value; and outputting said recalculated humidity value as the humidity value of said ambient air.

6. The method according to claim 5, further including the step of measuring the mass flow of said dehumidified air for use as a check to determine if the humidity value has been correctly calculated.

7. The method according to claim 5 wherein said extracting step is carried out by a dehumidifier which separates said captured airflow into a moisture flow and a dehumidified flow.

8. The method according to claim 7 wherein said step of calculating the humidity is carried out according to the following formula:

$$H_{n+1} = \eta_n * \frac{MM_n}{CM_n}$$

where $H_{n+1}$ is the calculated humidity, $MM_n$ is the moisture mass flow rate, $CM_n$ is the captured ambient air mass flow rate, and $\eta_n$ is the efficiency of the dehumidifier.

9. The method according to claim 8 wherein the efficiency of said dehumidifier varies based on the humidity of said ambient captured air and said efficiency is calculated based on said stored humidity value.

10. The method according to claim 5 wherein said captured air mass flow rate is measured by sensing a pressure difference in said captured airflow and using the following equation:

$$[CM]CM_n = K * \sigma * \Delta P$$

where $\sigma$ is a density correction factor, $\Delta P$ is a pressure difference, K is a calibrated constant, and n is a calibrated exponent.

11. The method according to claim 5 wherein said captured air mass flow rate is measured by sensing a flow meter radial velocity and using the following equation:

$$CM_n = K * \sigma * \omega$$

where $\omega$ is the radial velocity of the flow meter, $\sigma$ is a density correction factor, and K is a calibrated constant.

12. The method according to claim 5, further including:

storing said measured mass flow of said captured ambient air;

replacing said stored mass flow rate with said recalculated mass flow rate after said recalculating steps; and repeating said replacing step until said recalculated captured air mass flow rate approximately equals said stored captured air mass flow rate.

13. The method according to claim 12, further including:

measuring the mass flow of said dehumidified air;

calculating the mass flow of said dehumidified air based on said recalculated captured air and said measured mass flow of water extracted from said captured air; and outputting a signal if said measured value approximately equals said calculated value.

14. The method according to claim 5 wherein said recalculated humidity value is approximately equal to said stored humidity value if they are within a convergence criteria value of each other.

15. An apparatus for measuring the humidity of air surrounding an aircraft, comprising:

an air intake means for capturing a flow of air surrounding said aircraft;

an air mass flow rate measuring means for measuring the mass flow rate of said captured air;

a dehumidifier means for extracting moisture from said captured air;

a moisture mass flow rate measuring means for measuring the mass flow rate of said extracted moisture; and calculating means for calculating the humidity of said captured air using said captured air and said moisture mass flow rates as factors.

16. The apparatus according to claim 15 wherein said calculating means uses an assumed humidity value as a factor to measure the value of said captured air mass flow rate.

17. The apparatus according to claim 15, further including means for storing a first humidity value and means for storing a second humidity value.

18. The apparatus according to claim 15 wherein said air mass flow measuring means includes a pressure sensor.

19. The apparatus according to claim 15 wherein the efficiency of said dehumidifier varies according to the mass flow rate and the humidity of said captured air.

20. The apparatus according to claim 15 wherein the efficiency of said dehumidifier varies according to the mass flow rate, the humidity, the pressure, and temperature of said captured air.

21. A method for measuring the humidity of moist air external to a flying aircraft, comprising the steps of:

directing the moist air external to said aircraft to a dehumidifier within said aircraft via an air inlet while said aircraft is flying;

measuring the mass flow rate of the moist air;

dehumidifying said moist air with a dehumidifier to extract water;

measuring the mass flow rate of water extracted from said moist air by dehumidifying the moist air;

determining the humidity of the moist air from the moist air mass flow rate and water mass flow rate;

venting the water and dehumidified air; and outputting a signal indicative of the humidity of the moist air.

22. The method according to claim 21 wherein said step of determining the humidity of the moist air includes the steps of:

assuming a first humidity value of said moist air;

determining a first humidity value for the moist air from said measured flow rates and said assumed humidity value;

comparing said determined humidity value with said assumed humidity value; and replacing said assumed humidity value with said determined humidity value and repeating said determining step if said determined humidity is not approximately equal to said assumed humidity.

23. The method according to claim 21 wherein said measuring of the mass flow rate of said moist air requires solving an equation which includes the density of said moist air as one factor in the calculation.

24. An apparatus for measuring the humidity of air surrounding an aircraft while in flight, comprising:
an air intake coupled to said aircraft and directing a flow of moist air from external to said aircraft into said aircraft;
an air mass flow meter coupled to said aircraft and positioned aft of said air intake and within a flow path of moist air from said air intake;
a dehumidifier coupled aft of said air mass flow meter within said airflow path and extracting moisture from said moist air;
a moisture mass flow meter coupled aft of said dehumidifier and measuring the mass flow rate of the extracted moisture from said moist air; and
an electronic computer coupled to said mass flow meters and receiving said measured flow rates and to determine the humidity of said moist air external to said aircraft.

25. The apparatus according to claim 24 wherein said electronic computer includes a digital memory adapted to store the mass flow rates measured by said mass flow meters.

26. The apparatus according to claim 24 wherein said air mass flow meter includes a pressure sensor inserted into a flow of air from said air intake into said dehumidifier.

* * * * *